US008088392B2

(12) United States Patent
Cao

(10) Patent No.: US 8,088,392 B2
(45) Date of Patent: Jan. 3, 2012

(54) CAPSID PROTEINS AND USES THEREFORE

(75) Inventor: Yunxu Cao, Victoria (CA)

(73) Assignee: Yunxu Cao, Victoria, BC (CA)

( * ) Notice: Subject to any disclaimer, the term of this patent is extended or adjusted under 35 U.S.C. 154(b) by 48 days.

(21) Appl. No.: 12/140,415

(22) Filed: Jun. 17, 2008

(65) Prior Publication Data
US 2009/0181046 A1 Jul. 16, 2009

Related U.S. Application Data

(60) Provisional application No. 60/944,780, filed on Jun. 18, 2007.

(51) Int. Cl.
A61K 39/12 (2006.01)
A61K 39/29 (2006.01)
C12N 7/06 (2006.01)
(52) U.S. Cl. ............... 424/204.1; 424/184.1; 424/227.1; 435/235.1; 435/238
(58) Field of Classification Search ........................ None
See application file for complete search history.

(56) References Cited

U.S. PATENT DOCUMENTS

| 5,667,782 | A | 9/1997 | Roy |
| 6,887,464 | B1 | 5/2005 | Coleman et al. |
| 6,900,035 | B2 * | 5/2005 | Mizzen et al. ............... 435/69.7 |
| 6,962,777 | B1 | 11/2005 | McCarthy et al. |
| 7,205,125 | B2 | 4/2007 | Castillo et al. |
| 7,217,419 | B2 | 5/2007 | Wettendorff |
| 2010/0273237 | A1 * | 10/2010 | Kinzler et al. ............. 435/235.1 |

OTHER PUBLICATIONS

Devaraj et al. "Development of HPV vaccines for HPV-associated head and neck squamous cell carcinoma," Critical reviews in oral biology and medicine, vol. 14 No. 5, pp. 345-362 (2003).*
Tindle et al., "Chimeric Hepatitis B Core Antigen Particles Containing B- and Th-Epitopes of Human Papillomavirus Type 16 E7 Protein Induce Specific Antibody and T-Helper Responses in Immunised Mice," Virology, vol. 200 No. 2, pp. 547-557 (May 1994).*
Yang et al, "Recombinant heat shock protein 65 carrying hepatitis B core antigen induces HBcAg-specific CTL response.," Vaccine, vol. 25 No. 22, pp. 4478-4486 (May 2007).*
Aderem et al., Nature (2000) 406:782-787.
Beames et al., Journal of Virology (1995) 69(11):6833-6838.
Bhattacharyya et al., Biochemistry (2006) 45:3069-3076.
Bhuvanakantham et al., Biochemical and Biophysical Research Communications (2005) 329:246-255.
Birnbaum et al., Journal of Virology (1990) 64(7):3319-3330.
Buckle et al., PNAS USA (1997) 94(8):3571-3575.
Burel et al., Experientia (1992) 48:629-634.
Cella et al., J. Exp. Med. (1999) 189(5):821-829.
Chackerian, Expert Rev. Vaccines (2007) 6(3):381-390.
Chatellier et al., J. Mol. Biol. (1999) 292:163-172.
Chatellier et al., J. Mol. Biol. (2000) 304:879-910.
Chatellier et al., J. Mol. Biol. (2000) 304:883-896.
Chatellier et al., PNAS USA (1998) 95(17):9861-9866.
Chen et al., J. Mol. Biol. (2001) 307:173-182.
Chromy et al., PNAS USA (2003) 100(18):10477-10482.
Cobbald et al., Journal of Virology (2001) 75(16):7221-7229.
Cristofari et al., Nucleic Acids Research (2004) 32(8):2623-2631.
De Macario et al., Biochemical and Biophysical Research Communications (2003) 301:811-812.
Deuerling et al., Critical Reviews in Biochemistry and Molecular Biology (2004) 39:261-277.
Fox et al., Protein Science (2001) 10:622-630.
Fox et al., FEBS Letters (2003) 537:53-57.
Friede et al., Advanced Drug Delivery Reviews (2005) 57:325-331.
Ganea, Current Protein and Peptide Science (2001) 2:205-225.
Garcea et al., Current Opinion in Biotechnology (2004) 15:513-517.
GenBank accession No. M17705.1 (1993).
GenBank accession No. K02718.1 (1994).
GenBank accession No. AF324148.1 (2005).
Grgacic et al., Methods (2006) 40:60-65.
Griffiths et al., Journal of Virology (1993) 67(7):3191-3198.
Harris et al., Immunology (1992) 77:315-321.
Hartmann et al., PNAS USA (1999) 96(16):9305-9310.
Haslbeck, Cell. Moll. Life Sci. (2002) 59:1649-1657.
Houry, Current Protein and Peptide Science (2001) 2:227-244.
Hu et al., The EMBO Journal (1997) 16(1):59-68.
Hui et al., Journal of General Virology (1999) 80:2647-2659.
Hwang et al., Arch. Virol. (1998) 143:2203-2214.
Jacobs et al., Virology (1996) 219:339-349.
Jazayeri et al., Journal of Viral Hepatitis (2004) 11:488-501.
Jewett et al., J. Mol. Biol. (2006) 363:945-957.
Kegel et al., Biophysical Journal (2004) 86:3905-3913.
Kingsman et al., Annals New York Academy of Sciences (1995) 754:202-213.
Koschel et al., Journal of Virology (1999) 73(3):2153-2160.
Krieg, Current Opinion in Immunology (2000) 12:35-43.
Levy, Methods in Enzymology (1981) 78:242-251.
Li et al., The Journal of Biological Chemistry (2005) 280(5):3400-3406.
Liang et al., Current Drug Delivery (2006) 3:379-388.
Lin et al., Cancer Research (1996) 56:21-26.
Lingappa et al., The Journal of Cell Biology (1997) 136(3):567-581.
Lingappa et al., The Journal of Cell Biology (1994) 125(1):99-111.
Linger et al., RNA (2004) 10:128-138.
Ma et al., Protein Engineering (2000) 13(9):617-627.
Macario et al., Frontiers in Bioscience (2001) 6:262-283.
Macario et al., Frontiers in Bioscience (2004) 9:1318-1332.
Macario et al., Frontiers in Bioscience (2007) 12:2588-2600.
Macario, Int. J. Clin. Lab. Res. (1995) 25:59-70.
Macario et al., J. Mol. Evol. (2006) 63:74-86.
Macario et al., Microbiology and Molecular Biology Reviews (1999) 63(4):923-967.
Macario et al., Stress (1997) 1(3):123-134.
Macejak et al., Journal of Virology (1992) 66(3):1520-1527.
Maeder et al., J. Mol. Evol. (2005) 60:409-416.
Mayer et al. In: Advances in Protein Chemistry, vol. 59, Academic Press (2002) pp. 1-44.

(Continued)

Primary Examiner — Stacy B. Chen

(57) ABSTRACT

The present invention provides methods for the use of viral capsid proteins and chaperone proteins to produce immunogenic macro-molecular structures as antigen carrier to carry desired epitopes or antigens, for enhancing the immunogenicity of the carried epitopes or antigens for therapeutic or prophylactic vaccination. The immunogenic macro-molecular structures may also be used for therapeutic or prophylactic vaccination.

41 Claims, No Drawings

OTHER PUBLICATIONS

Mayer et al., Biol. Chem. (2000) 381:877-885.
Milich et al., Science (1986) 234(4782)1398-1401.
Morellet et al., Protein Science (2005) 14:375-386.
Mukhopadhyay et al., Journal of Virology (2002) 76(21):11128-11132.
Muriaux et al., PNAS USA (2001) 98(9):5246-5251.
Noad et al., TRENDS in Microbiology (2003) 11(9):438-444.
Novagen Catalogue, pET-23(+) Vector, TB064, Dec. 1998.
Ohtsuka et al., Int. J. Hyperthermia (2000) 16(3):231-245.
Paintsil et al., Virology (1996) 223:238-244.
Pattenden et al., TRENDS in Biotechnology (2005) 23(10):523-529.
pBluescript II Phagemid Vectors, Instruction Manual, Agilent Technologies, Inc. (2008).
Pearl et al. in: Advances in Protein Chemistry, vol. 59, Academic Press (2002) pp. 157-186.
Pumpens et al., FEBS Letters (1999) 442:1-6.
Pumpens et al., Intervirology (2001) 44:98-114.
Ramon-Luing et al., Biotechnology Letters (2006) 28:301-307.
Raychaudhuri et al., Nature Biotechnology (1998) 16:1025-1031.
Reguera et al., The Journal of Biological Chemistry (2005) 280(18):17969-17977.
Riedl et al., J. Immunol. (2002) 168:4951-4959.
Roseman et al., PNAS USA (2005) 102(44):15821-15826.
Sandovici et al., Rev. Med. Chir. Soc. Med. Nat. (1999) 103(3-4):35-43 (abstract).
Schodel et al., Intervirology (1996) 39:104-110.
Scholl et al., Journal of Controlled Release (2005) 104:1-27.
Sedlik et al., PNAS USA (1997) 94:7503-7508.
Stan et al., Biophysical Chemistry (2003) 100:453-467.
Stirling et al., EMBO Reports (2003) 4(6):565-570.
Storni et al., Advanced Drug Delivery Reviews (2005) 57:333-355.
Sullivan et al., Virology (2001) 287:1-8.
Sun et al., Cell. Mol. Life Sci. (2005) 62:2460-2476.
Taguchi et al., The Journal of Biological Chemistry (1994) 269(11):8529-8534.
Tellinghuisen et al., Journal of Virology (1999) 73(7):5309-5319.
Tellinghuisen et al., Journal of Virology (2000) 74(9):4302-4309.
Thole et al., Infection and Immunity (1987) 55(6):1466-1475.
Tsumoto et al., Protein Engineering (2003) 16(7):535-541.
Ulrich et al. in: Advances in Virus Research, vol. 50, Academic Press, New York, NY (1998) pp. 141-182.
Verdijk et al., J. Immunol. (1999) 163:57-61.
Walter, Cell. Mol. Life Sci. (2002) 59:1589-1597.
Weiner, Curr. Top. Microbiol. Immunol. (2000) 247:157-170.
Wengler et al., Virology (1984) 132:401-412.
Wilkinson et al., Biochemistry (2005) 44:2800-2810.
Xu et al., Arch. Virol. (2006) 151:2133-2148.
Yamamoto et al., Jpn. J. Cancer Res. (1994) 85:775-779.
Yao et al., Journal of Virology (1996) 70(11):7910-7920.

* cited by examiner

CAPSID PROTEINS AND USES THEREFORE

CROSS-REFERENCE TO RELATED APPLICATIONS

This application claims the priority from the provisional application U.S. Ser. No. 60/944,780, filed on 18 Jun. 2007.

REFERENCES CITED

1. Chackerian B. 2007. Virus-like particles: flexible platforms for vaccine development. *Expert Rev Vaccines.* 6(3):381-90.
2. Grgacic E V, Anderson D A. 2006. Virus-like particles: passport to immune recognition. *Methods.* 40(1):60-5.
3. U.S. Pat. No. 7,205,125. Mixed Virus-like particles
4. U.S. Pat. No. 7,217,419. Vaccine composition comprising virus-like particles of human papillomavirus
5. U.S. Pat. No. 6,887,464. Advanced antigen presentation platform
6. U.S. Pat. No. 5,677,782. Multiple particulate antigen delivery system
7. Xu Y F, Zhang Y Q, Xu X M, Song G X. 2006. Papillomavirus virus-like particles as vehicles for the delivery of epitopes or genes. *Arch Virol.* 151(11):2133-48.
8. Pattenden L K, Middelberg A P, Niebert M, Lipin D I. 2005. Towards the preparative and large-scale precision manufacture of virus-like particles. *Trends Biotechnol.* 23(10): 523-9.
9. Garcea R L, Gissmann L. 2004. Virus-like particles as vaccines and vessels for the delivery of small molecules. *Curr Opin Biotechnol.* 15(6):513-7.
10. Noad R, Roy P. 2003. Virus-like particles as immunogens. *Trends Microbiol.* 11(9):438-44.
11. Sedlik C, Saron M, Sarraseca J, Casal I, Leclerc C. 1997. Recombinant parvovirus-like particles as an antigen carrier: a novel nonreplicative exogenous antigen to elicit protective antiviral cytotoxic T cells. *Proc. Natl. Acad. Sci. USA.* 94(14):7503-8.
12. Ulrich R, Nassal M, Meisel H, Kruger D H. 1998. Core particles of hepatitis B virus as carrier for foreign epitopes. *Adv Virus Res.* 50:141-82
13. Pumpens P, Grens E. 1999. Hepatitis B core particles as a universal display model: a structure-function basis for development. *FEBS Lett. January* 8; 442(1):1-6
14. Pumpens P, Grens E. 2001. HBV core particles as a carrier for B cell/T cell epitopes. *Intervirology.* 44(2-3):98-114.
15. Riedl P, Stober D, Oehninger C, Melber K, Reimann J, Schirmbeck R. 2002. Priming Th1 immunity to viral core particles is facilitated by trace amounts of RNA bound to its arginine-rich domain. *J Immunol.* 168(10):4951-9
16. Hu J, Toft D O, Seeger C. 1997. Hepadnavirus assembly and reverse transcription require a multi-component chaperone complex which is incorporated into nucleocapsids. *EMBO J.* 16(1):59-68.
17. Macejak D G, Sarnow P. 1992. Association of Heat Shock Protein 70 with Enterovirus Capsid Precursor P1 in Infected Human Cells *J. Virol.* 66(3):1520-1527.
18. Wilkinson T A, Tellinghuisen T L, Kuhn R J, Post C B. 2005. Association of sindbis virus capsid protein with phospholipid membranes and the E2 glycoprotein: implications for alphavirus assembly. *Biochemistry.* 44(8):2800-10
19. Lingappa J R, Martin R L, Wong M L, Ganem D, Welch W J, Lingappa V R. 1994. A eukaryotic cytosolic chaperonin is associated with a high molecular weight intermediate in the assembly of hepatitis B virus capsid, a multimeric particle. *J Cell Biol.* 125(1):99-111.
20. Wilkinson T A, Tellinghuisen T L, Kuhn R J, Post C B. 2005. Association of sindbis virus capsid protein with phospholipid membranes and the E2 glycoprotein: implications for alphavirus assembly. *Biochemistry.* 44(8):2800-10
21. U.S. Pat. No. 6,962,777. In vitro method for disassembly/reassembly of papillomavirus virus-like particles (VLPs).
22. Cobbold C, Windsor M, Wileman T. 2001. A Virally Encoded Chaperone Specialized for Folding of the Major Capsid Protein of African Swine Fever Virus. *J. Virol.* 75(16):7221-7229.
23. Hwang D, Turner N, Wilson T. 1998. Chaperone protein GrpE and the GroEL/GroES complex promote the correct folding of tobacco mosaic virus coat protein for ribonucleocapsid assembly in vivo. *Arch Virol.* 143(11):2203-14.
24. Chromy L, Pipas J, Garcea R. 2003. Chaperone-mediated in vitro assembly of Polyomavirus capsids. *Proc. Nall. Acad. Sci. USA.* 100(18):10477-10482
25. Sullivan C S, Pipas J M. 2001. The virus-chaperone connection. *Virology.* 287(1):1-8.
26. Muriaux, D., Mirro, J., Harvin, D., Rein, A. 2001. RNA is a structural element in retrovirus particles. *Proc. Natl. Acad. Sci. USA* 98: 5246-5251
27. LINGER, B. R., KUNOVSKA, L., KUHN, R. J., GOLDEN, B. L. 2004. Sindbis virus nucleocapsid assembly: RNA folding promotes capsid protein dimerization. *RNA* 10: 128-138
28. Mukhopadhyay, S., Chipman, P. R., Hong, E. M., Kuhn, R. J., Rossmann, M. G. 2002. In Vitro-Assembled Alphavirus Core-Like Particles Maintain a Structure Similar to That of Nucleocapsid Cores in Mature Virus. *J. Virol.* 76: 11128-11132
29. Tellinghuisen, T. L., Kuhn, R. J. (2000). Nucleic Acid-Dependent Cross-Linking of the Nucleocapsid Protein of Sindbis Virus. *J. Virol.* 74: 4302-4309
30. Yao, J. S., E. G. Strauss, and J. H. Strauss. 1996. Interactions between PE2, E1, and 6K required for assembly of alphaviruses studied with chimeric viruses. *J. Virol.* 70:7910-7920
31. Lingappa J R, Hill R L, Wong M L, Hegde R S. 1997. A multistep, ATP-dependent pathway for assembly of human immunodeficiency virus capsids in a cell-free system. *J Cell Biol.* 136(3):567-81.
32. Wengler, G., G. Wengler, U. Boege, and K. Wahn. 1984. Establishment and analysis of a system which allows assembly and disassembly of alphavirus core-like particles under physiological conditions in vitro. *Virology* 132:401-412
33. Tellinghuisen T L, Hamburger A E, Fisher B R, Ostendorp R, Kuhn R J. 1999. In vitro assembly of alphavirus cores by using nucleocapsid protein expressed in *Escherichia coli. J Virol.* 73(7):5309-19.
34. Cristofari G, Ivanyi-Nagy R, Gabus C, Boulant S, Layergne J P, Penin F, Darlix J L. 2004. The hepatitis C virus Core protein is a potent nucleic acid chaperone that directs dimerization of the viral (+) strand RNA in vitro. *Nucleic Acids Res.* 32(8):2623-31.
35. Birnbaum F, Nassal M. 1990. Hepatitis B virus nucleocapsid assembly: primary structure requirements in the core protein. *J Virol.* 64(7):3319-30.
36. Chen X S, Casini G, Harrison S C, Garcea R L. 2001. Papillomavirus capsid protein expression in *Escherichia coli*: purification and assembly of HPV11 and HPV16 L1. *J Mol Biol.* 307(1):173-82.

37. Hui E K, Yi Y S, Lo S J. 1999. Hepatitis B viral core proteins with an N-terminal extension can assemble into core-like particles but cannot be enveloped. *J Gen Virol.* 80 (Pt 10):2647-59.
38. Deuerling E, Bukau B. 2004. Chaperone-assisted folding of newly synthesized proteins in the cytosol. *Crit Rev Biochem Mol Biol.* 39(5-6):261-77.
39. Walter S. 2002. Structure and function of the GroE chaperone. *Cell Mol Life Sci.* 59(10):1589-97.
40. Houry W A. 2001. Chaperone-assisted protein folding in the cell cytoplasm. *Curr Protein Pept Sci.* 2(3):227-44.
41. Pearl L H, Prodromou C. 2001. Structure, function, and mechanism of the Hsp90 molecular chaperone. *Adv Protein Chem.* 59:157-86.
42. Mayer M P, Brchmer D, Gassier C S, Bukau B. 2001. Hsp70 chaperone machines. *Adv Protein Chem.* 59:1-44.
43. Macario A J, Conway De Macario E. 2001. The molecular chaperone system and other anti-stress mechanisms in archaea. *Front Biosci.* 6:D262-83.
44. Mayer M P, Rudiger S, Bukau B. 2000. Molecular basis for interactions of the DnaK chaperone with substrates. *Biol Chem.* 381(9-10):877-85.
45. Ma B, Tsai C J, Nussinov R. 2000. Binding and folding: in search of intramolecular chaperone-like building block fragments. *Protein Eng.* 13(9):617-27
46. Ohtsuka K, Hata M. 2000. Molecular chaperone function of mammalian Hsp70 and Hsp40-a review. *Int J Hyperthermia.* 16(3):231-45.
47. Sandovici I, Bostaca I. 1999. Chaperone proteins—essential proteins for cellular activity. *Rev Med Chir Soc Med Nat Iasi.* 103(3-4):35-43.
48. Macario A J. 1995. Heat-shock proteins and molecular chaperones: implications for pathogenesis, diagnostics, and therapeutics. *Int J Clin Lab Res.* 25(2):59-70.
49. Burel C, Mezger V, Pinto M, Rallu M, Trigon S, Morange M. 1992. Mammalian heat shock protein families. Expression and functions. *Experientia.* 48(7):629-34.
50. Macario A J, Conway de Macario E. 2007. Molecular chaperones: multiple functions, pathologies, and potential applications. *Front Biosci.* 12:2588-600.
51. Macario A J, Brocchieri L, Shenoy A R, de Macario E C. 2006. Evolution of a protein-folding machine: genomic and evolutionary analyses reveal three lineages of the archacal hsp70(dnaK) gene. *J Mol Evol.* 63(1):74-86.
52. Maeder D L, Macario A J, de Macario E C. 2005. Novel chaperonins in a prokaryote. *J Mol Evol.* 60(3):409-16.
53. Conway de Macario E, Maeder D L, Macario A J. 2003. Breaking the mould: archaea with all four chaperoning systems. *Biochem Biophys Res Commun.* 301(4):811-2.
54. Macario A J, Lange M, Ahring B K, De Macario E C. 1999. Stress genes and proteins in the archaca. *Microbiol Mol Biol Rev.* 63(4):923-67.
55. Macario A J, Conway de Macario E. 1997. Mini-Review; Stress Genes: An Introductory Overview. *Stress.* 1(3):123-134.
56. Macario A J, Malz M, Conway de Macario E. 2004. Evolution of assisted protein folding: the distribution of the main chaperoning systems within the phylogenetic domain archaea. *Front Biosci.* 9:1318-32.
57. Ganea E. 2001. Chaperone-like activity of alpha-crystallin and other small heat shock proteins. *Curr Protein Pept Sci.* 2(3):205-25.
58. Sun Y, MacRae T H. 2005. Small heat shock proteins: molecular structure and chaperone function. *Cell Mol Life Sci.* 62(21):2460-76.
59. Haslbeck M. 2002. sHsps and their role in the chaperone network. *Cell Mol Life Sci.* 59(10):1649-57.
60. Harris S J, Gearing A J, Layton G T, Adams S E, Kingsman A J. 1992. Enhanced proliferative cellular responses to HIV-1 V3 peptide and gp120 following immunization with V3:Ty virus-like particles. *Immunology.* 77(3):315-21.
61. Griffiths J C, Harris S J, Layton G T, Berrie E L, French T J, Burns N R, Adams S E, Kingsman A J. 1993. Hybrid human immunodeficiency virus Gag particles as an antigen carrier system: induction of cytotoxic T-cell and humoral responses by a Gag:V3 fusion. *J Virol.* 67(6):3191-8.
62. Schöll I, Boltz-Nitulescu G, Jensen-Jarolim E. 2005. Review of novel particulate antigen delivery systems with special focus on treatment of type I allergy. *J Control Release.* 104(1): 1-27
63. Liang M T, Davies N M, Blanchfield J T, Toth I. 2006. Particulate systems as adjuvants and carriers for peptide and protein antigens. *Curr Drug Deliv.* 3(4):379-88.
64. Storni T, Kundig T M, Senti G, Johansen P. 2005. Immunity in response to particulate antigen-delivery systems. *Adv Drug Deliv Rev.* 57(3):333-55.
65. Friede M, Aguado M T. 2005. Need for new vaccine formulations and potential of particulate antigen and DNA delivery systems. *Adv Drug Deliv Rev.* 57(3):325-31.
66. Kingsman A J, Burns N R, Layton G T, Adams S E. 1995. Yeast retrotransposon particles as antigen delivery systems. *Ann N Y Acad Sci.* 754:202-13
67. Schodel F, Peterson D, Milich D. 1996. Hepatitis B virus core and c antigen: immune recognition and use as a vaccine carrier moiety. *Intervirology.* 39(1-2):104-10
68. Raychaudhuri S, Rock K L. 1998. Fully mobilizing host defense: building better vaccines. *Nat Biotechnol.* 16(11): 1025-31.
69. Roseman A M, Berriman J A, Wynne S A, Butler P J, Crowther R A. 2005. A structural model for maturation of the hepatitis B virus core. *Proc Natl Acad Sci USA.* 102 (44):15821-6.
70. Kegel W K, Schoot Pv P. 2004. Competing hydrophobic and screened-coulomb interactions in hepatitis B virus capsid assembly. *Biophys J.* 86(6):3905-13.
71. Li S W, Zhang J, He Z Q, Gu Y, Liu R S, Lin J, Chen Y X, Ng M H, Xia N S. 2005. Mutational analysis of essential interactions involved in the assembly of hepatitis E virus capsid. *J Biol Chem.* 280(5):3400-6.
72. Morellet N, Druillennec S, Lenoir C, Bouaziz S, Rogues B P. 2005. Helical structure determined by NMR of the HIV-1 (345-392) Gag sequence, surrounding p2: implications for particle assembly and RNA packaging. *Protein Sci.* 14(2):375-86.
73. Bhuvanakantham R, Ng M L. 2005. Analysis of self-association of West Nile virus capsid protein and the crucial role played by Tip 69 in homodimerization. *Biochem Biophys Res Commun.* 329(1):246-55
74. Reguera J, Grueso E, Carreira A, Sanchez-Martinez C, Almendral J M, Mateu M G. 2005. Functional relevance of amino acid residues involved in interactions with ordered nucleic acid in a spherical virus. *J Biol Chem.* 280(18): 17969-77.
75. Krieg A M. 2000. The role of CpG motifs in innate immunity. *Curr. Opin. Immunol.* 12:35.
76. Jacobs B L, Langland J O. 1996. When two strands are better than one: the mediators and modulators of the cellular responses to double-stranded RNA. *Virology* 219: 339.
77. Hartmann G. G, Weiner J, Krieg A M. 1999. CpG DNA: a potent signal for growth, activation, and maturation of human dendritic cells. *Proc. Natl. Acad. Sci. USA* 96:9305.

78. Cella M, Salio M, Sakakibara Y, Langen H, Julkunen I, Lanzavecchia A. 1999. Maturation, activation, and protection of dendritic cells induced by double-stranded RNA. *J. Exp. Med.* 189:821.
79. Verdijk R, Mutis M T, Esendam B, Kamp J, Melief C J, Brand A, Goulmy E. 1999. Polyriboinosinic polyribocytidylic acid (poly(I:C)) induces stable maturation of functionally active human dendritic cells. *J. Immunol.* 163:57.
80. Yamamoto T, Yamamoto S, Kataoka T, Komuro K, Kohase M, Tokunaga T. 1994. Synthetic oligonucleotides with certain palindromes stimulate interferon production of human peripheral blood lymphocytes in vitro. *Jpn. J. Cancer Res.* 85:775.
81. Levy HB. 1981. Induction of interferon in vivo and in vitro by polynucleotides and derivatives, and preparation of derivatives. *Methods Enzymol.* 78:242.
82. Weiner G J. 2000. CpG DNA in cancer immunotherapy. *Curr. Top. Microbiol. Immunol.* 247:157.
83. Aderem A, Ulevitch R J. 2000. Toll-like receptors in the induction of the innate immune response. *Nature* 406:782.
84. Thole J E, Keulen W J, De Bruyn J, Kolk A H, Groothuis D G, Berwald L G, Tiesjema R H, van Embden J D. 1987. Characterization, sequence determination, and immunogenicity of a 64-kilodalton protein of *Mycobacterium bovis* BCG expressed in *escherichia coli* K-12. *Infect Immun.* 55(6):1466-75.
85. Jazayeri M, Basuni A A, Sran N, Gish R, Cooksley G, Locarnini S, Carman W F. 2004. HBV core sequence: definition of genotype-specific variability and correlation with geographical origin. *J Viral Hepat.* 11(6):488-501.
86. http://www.ncbi.nlm.nih.gov/ (NCBI Nucleotide Accession AF324148, GI: 16930339) for core protein.
87. HPV-16-E7 (GenBank accession #K02718)
88. pBluescript II SK (+/−): (http://www.stratagene.com/vectors/maps/pdf/pBluescript%20II%20SK+_%20webpg-.pdf)
89. pET-23a: (http://www.emdbiosciences.com/docs/docs/PROT/TB051.pdf)
90. Lin K Y, Guarnieri F G, Staveley-O'Carroll K F, Levitsky H I, August J T, Pardoll D M, Wu T C. 1996. Treatment of established tumors with a novel vaccine that enhances major histocompatibility class II presentation of tumor antigen. *Cancer Res.* 56(1):21-6.
91. Jewett A I, Shea J E. 2006. Folding on the chaperone: yield enhancement through loose binding. *J Mol Biol.* 363(5):945-57.
92. Buckle A M, Zahn R, Fersht A R. 1997. A structural model for GroEL-polypeptide recognition. *Proc Natl Acad Sci USA.* 94(8):3571-5.
93. Stan G, Thirumalai D, Lorimer G H, Brooks B R. 2003. Annealing function of GroEL: structural and bioinformatic analysis. *Biophys Chem.* 100(1-3):453-67.
94. Tsumoto K, Umetsu M, Yamada H, Ito T, Misawa S, Kumagai I. 2003. Immobilized oxidoreductase as an additive for refolding inclusion bodies: application to antibody fragments. *Protein Eng.* 16(7):535-41.
95. Bhattacharyya J, Padmanabha Udupa E G, Wang J, Sharma K K. 2006. Mini-alphaB-crystallin: a functional element of alphaB-crystallin with chaperone-like activity. *Biochemistry.* 45(9):3069-76.
96. Ramon-Luing L A, Cruz-Migoni A, Ruiz-Medrano R, Xoconostle-Cazares B, Ortega-Lopez J. 2006. One-step purification and immobilization in cellulose of the GroEL apical domain fused to a carbohydrate-binding module and its use in protein refolding. *Biotechnol Lett.* 28(5):301-7.
97. Fox J D, Routzahn K M, Bucher M H, Waugh D S. 2003. Maltodextrin-binding proteins from diverse bacteria and archaea are potent solubility enhancers. *FEBS Lett.* 537(1-3):53-7.
98. Fox J D, Kapust R B, Waugh D S. 2001. Single amino acid substitutions on the surface of *Escherichia coli* maltose-binding protein can have a profound impact on the solubility of fusion proteins. *Protein Sci.* 10(3):622-30.
99. Chatellier J, Hill F, Foster N R, Goloubinoff P, Fersht A R. 2000. From minichaperone to GroEL 3: properties of an active single-ring mutant of GroEL. *J Mol Biol.* 304(5):897-910.
100. Chatellier J, Hill F, Fersht A R. 2000. From minichaperone to GroEL 2: importance of avidity of the multisite ring structure. *J Mol Biol.* 304(5):883-96.
101. Chatellier J, Buckle A M, Fersht A R. 1999. GroEL recognises sequential and non-sequential linear structural motifs compatible with extended beta-strands and alpha-helices. *J Mol Biol.* 292(1): 163-72.
102. Chatellier J, Hill F, Lund P A, Fersht A R. 1998. In vivo activities of GroEL mini chaperones. *Proc Natl Acad Sci USA.* 95(17):9861-6.
103. Stirling P C, Lundin V F, Leroux M R. 2003. Getting a grip on non-native proteins. *EMBO Rep.* 4(6):565-70.
104. Taguchi H, Makino Y, Yoshida M. 1994. Monomeric chaperonin-60 and its 50-kDa fragment possess the ability to interact with non-native proteins, to suppress aggregation, and to promote protein folding. *J Biol Chem.* 269(11): 8529-34.
105. Kedzierska S. 2005. Role of *Escherichia coli* molecular chaperones in the protection of bacterial cells against irreversible aggregation induced by heat shock Postepy *Biochem.* 51(2): 146-53.
106. Koschel M, Thomssen R, Bruss V. 1999. Extensive mutagenesis of the hepatitis B virus core gene and mapping of mutations that allow capsid formation. *J Virol.* 73(3): 2153-60.
107. Paintsil J, Muller M, Picken M, Gissmann L, Zhou J. 1996. Carboxyl terminus of bovine papillomavirus type-1 L1 protein is not required for capsid formation. *Virology.* 223(1):238-44.
108. Beames B, Lanford R E. 1995. Insertions within the hepatitis B virus capsid protein influence capsid formation and RNA encapsidation. *J Virol.* 69(11):6833-8.
109. Milich D R, McLachlan A. 1986. The nucleocapsid of hepatitis B virus is both a T-cell-independent and a T-cell-dependent antigen. *Science.* 234(4782):1398-401.
110. Hsp65 (GenBank Accession: M17705.1 GI:149933)

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 655982000300Seqlist.txt | Aug. 3, 2010 | 773 bytes |

FIELD OF THE INVENTION

The present invention relates to the development of immunogenic compositions for therapeutic and prophylactic vaccinations.

BACKGROUND OF THE INVENTION

A variety of virus capsid proteins have the intrinsic ability to self-assemble into highly organized particles. By using recombinant DNA techniques, capsid proteins can be recombinantly produced from different hosts such as mammalian cells, insect cells, yeast and E. coli. Often, the produced capsid proteins can self-assemble into particles in the hosts that closely resemble virions. The resulted particles are called virus-like particles (VLPs). Because of lacking viral genome, VLPs are nonreplicating and noninfectious (1-14).

There are numerous documented research work and granted patents in the area of using VLPs prepared from virus capsid proteins as vaccines or using VLPs as antigen carriers or antigen delivery systems (or vehicles) to carry desired epitopes or antigens, in efforts to enhance the immunogenicity of the carried epitopes or antigens, and to prime in vivo class I-restricted cytotoxic responses (1-14, 62-68). Most of the antigen-delivery systems are formulated in particles or particulate in nature. A variety of materials, including lipids, proteins, polysaccharides, polyacrylic substances or organic acids are formulated into particles to serve as antigen delivery systems. Among them, capsid proteins formed virus-like-particles (VLPs) represent prime candidates as antigen carriers for the delivery of heterologous antigens for other diseases because of the ideal size of their particles, simplicity and the ability to induce desirable type of immune response (62-68). Also, the relative immunogenicity of different particulate antigen-delivery systems can be very different, capsid protein based particulate antigen-delivery systems may be more immunogenic than other particulate antigen-delivery systems (62-68, 109).

There is no doubt that VLPs can be expressed abundantly in a variety of expression systems by recombinant DNA techniques. There are very little doubts to the prophylactic or therapeutic potentials of using VLPs as vaccines or using them as antigen carriers for eliciting enhanced immune responses, particularly cell-mediated immune response against carried antigens or epitopes. Due to their particulate nature, VLPs usually can be purified in particles by methods such as salt precipitation with ammonium sulfate, density gradient centrifugation, and gel filtration. However, to use this technology to produce medicines, in particular for use in humans, there are still unsolved problems related to the economically and reproducibly preparing intact homogeneous particles from expression host systems with well defined compositions able to withstand long-term storage (8).

When produced by recombinant DNA technology, VLPs like many other recombinant proteins will be contaminated with host proteins, lipids, nucleic acids et al. These contaminations have to be removed to very low levels to meet the requirements for medical application. However, the removal of the contaminations from VLPs is complicated due to the fact that when VLPs are expressed and assembled in the expression systems, the host proteins and lipids can be incorporated into the VLPs and host nucleic acids can be packaged into the VLPs (15-20). Purification of whole VLPs will not be able to remove these incorporated or packaged contaminations. More ever, VLPs are super-molecular structures with molecular weight normally exceeds 10.00 Kd, Possibly due to the poor mass transfer in chromatographic processes because of the VLPs' massive sizes compare to monomer proteins or other small molecules, when the separations are conducted by using absorbent resins, the binding, elution and fractionation are not as effective and efficient as smaller molecules.

The importance of being able to purifying totally dissembled capsid proteins are noted in U.S. Pat. No. 6,962,777 and others (8, 21). VLPs' assembly requires correctly-folded capsid proteins to start with. Under non-denaturing conditions, the in vitro method for the quantitative disassembly and subsequent reassembly of VLPs is highly specific for each individual capsid protein and U.S. Pat. No. 6,962,777 might be the only published work dealt with this issue with VLPs prepared from human papillomavirus (HPV) L1 major capsid protein. Many factors significant for VLPs formation and stability have not been well elucidated. It is generally known that VLPs' disassembly and assembly can be affected by numerous factors. For example, pH, ionic strength, post-translational modifications of viral capsid proteins, disulfide bonds, and divalent cation bonding. To make this issue even more complicated is that the VLPs' disassembly and assembly often require chaperones participation and for some VLPs formation, certain specific structure nucleic acids are required (8, 21-36). Thus, there are numerous interrelated factors which may affect capsid stability, assembly and disassembly in vitro, which vary widely even for related viruses. Furthermore, the tendency of forming aggregates by partially dissembled or totally dissembled capsid proteins is another major obstacles in the process of producing homogenous and stable VLPs effectively and efficiently in vitro (8).

To simply dissemble VLPs, high concentration of Chaotropic agents such as urea or guanidine hydrochloride (Gu. HCl) can be used, as these agents will disrupt non-covalent forces such as hydrogen bonds, Van der Waals interactions, and the hydrophobic interactions in the capsid proteins, and the disulfide bonds in capsid proteins can be disrupted simply by reducing agents or oxidative sulfitolysis process. If just for producing pure capsid proteins, then to subject VLPs in high concentration of Gu.HCl and urea, plus necessary reagents to disrupt disulfide bonds in the purification process would be advantageous because of the following reasons. (1) Capsid proteins are much less likely to form aggregates in high concentration of urea or Gu.HCl, so the purification process can be much more efficient and scalable; (2) High concentration of urea or Gu.HCl can weak the interactions (hydrogen bonding, Van der Waals interactions, and the hydrophobic effect) between capsid proteins and contaminations; so the purification process can be much more effective in terms at removing contaminations; (3) VLPs are disintegrated in the high concentration of urea or Gu.HCl, so the capsid proteins exhibit more homogenous properties in the purification process; (4) disintegrated VLPs are much more likely to release or expose incorporated or packaged contaminations to the purification forces for removing them. However, the chaotropic agents such as urea or Gu.HCl are also strong protein denaturants, proteins are denatured after the treatment with high concentration of urea or Gu.HCl, and there is still lack of knowledge on how to correctly refold denatured capsid proteins. If denatured capsid proteins are not correctly refolded, they often form aggregates instead of self-assemble into VLPs (8, 21).

A host's immune responses or immune tolerance to a virus may also pose problems for using authentic VLPs as antigen carriers. Capsid proteins formed VLPs represent prime candidates as antigen carriers for the delivery of heterologous antigens because of the ideal size of their particles, simplicity and the ability to induce desirable type of immune response (62-68). However, the host might have been infected with the viruses, and the infections may result the host developing immune responses to the VLPs prepared from the same viruses or close related viruses; or the infection may result host developing immune tolerance to the VLPs prepared from the same viruses or close related viruses. In either case, the effectiveness of using VLPs as antigen carriers in such host will be greatly reduced.

It can be advantages if capsid proteins with self-assembly ability can be utilized to prepare particles (macro-molecular structures) with different morphology from the authentic VLPs as antigen carriers. Because of the differences of the morphology, the macro-molecular structures will display or expose a different set of epitope peptides compare to authentic VLPs, and may have the following advantages over authentic VLPs: (1) pre-existing immunity to authentic VLPs might be circumvented by the use of macro-molecular structures with different morphology; (2) existing immune tolerance to authentic capsid proteins might be circumvented by the use of the macro-molecular structures with different morphology; (3) the use of macro-molecular structures with different morphology might circumvent the problem of interference with commercial anti-capsid protein assays.

Therefore, there exists a need in the art for a general method, which would conduct the purification of recombinantly expressed capsid proteins in one or more steps in high concentration of chaotropic agents (denaturing conditions) plus necessary agents to disrupt disulfide bonds, then refold and reassemble of purified homogenous capsid proteins. There also exists a need in the art to utilize capsid proteins to prepare particles (macro-molecular structures) morphologically different from authentic VLPs as antigen carriers for circumventing pre-existing immune responses to the VLPs or existing immune tolerance to the VLPs.

SUMMARY OF THE INVENTION

The present invention relates to prepare immunogenic macro-molecular structures by utilizing capsid proteins intrinsic self-assembly ability and chaperone proteins ability to bind and prevent denatured proteins from aggregations and facilitate their folding.

In this invention, the said macro-molecular structures are prepared from a fusion protein comprising a virus capsid (or nucleocapsid) protein and a chaperone protein. The said fusion protein is named as FCCP. The said FCCP is recombinantly produced, and is purified in denatured form in high concentration of chaotropic agent solution. The denatured FCCP is refolded and re-assembled into the macro-molecular structures.

One of the major objects of this invention is to use the macro-molecular structures derived from FCCP instead of the VLPs derived from capsid proteins as antigen or epitope carriers for enhancing the immunogenicity of the carried epitopes or antigens for therapeutic or prophylactic vaccination.

The compositions of the macro-molecular structures derived from FCCP carrying heterologous antigen or epitope can be prepared by (1) chemically linking or conjugating heterologous antigen or epitope to the FCCP, or to the macro-molecular structures derived from FCCP; (2) linking heterologous antigen or epitope to the FCCP via a peptide bond to form a single fusion protein comprising said heterologous antigen and said FCCP, then recombinantly producing heterologous antigen-FCCP fusion protein, purifying heterologous antigen-FCCP fusion protein in denatured form, refolding and re-assembling denatured heterologous antigen-FCCP fusion protein into macro-molecular structures.

In this invention, the compositions of the macro-molecular structures derived from FCCP carrying heterologous antigen may be used for therapeutic or prophylactic vaccination by inducing desirable immune responses, particularly a cell-mediated immune response against carried antigen.

The use of macro-molecular structures instead of authentic VLPs may have the following advantages: (1) pre-existing immunity to authentic VLPs might be circumvented by the use of macro-molecular structures with different morphology; (2) existing immune tolerance to authentic capsid proteins might be circumvented by the use of the macro-molecular structures with different morphology; (3) the use of macro-molecular structures with different morphology might circumvent the problem of interference with commercial anti-capsid protein assays.

DETAILED DESCRIPTION OF THE INVENTION

As the refolding and reassembly of capsid proteins are affected by many factors, most of them are not well defined and some of the factors are still unknown, it will be difficult to refold and reassemble denatured capsid proteins if some of the related factors are unknown or not well defined. To overcome this problem, a fusion capsid-chaperone protein (FCCP) has been designed based on the following reasons: (1) virus capsid proteins have the intrinsic ability to self-assemble into particles; (2) virus capsid proteins can accommodate certain length of peptide fused to its N-terminal or C-terminal and still retain the ability of self-assembling into particles (12, 12, 36-37); (3) chaperone proteins can bind and prevent non-native or denatured proteins from aggregations and facilitate their folding (38-59, 103-104); (4) when exogenous antigens are particulate in nature, they are presented 1,000 or 10,000-fold more efficiently than soluble antigen in both class I and class II pathways (5, 60-68). The FCCP is composed with a capsid protein and a chaperone protein, the chaperone protein is linked to capsid protein to its N-terminal or C-terminal via a peptide bond to form a single molecule. The objects of this designed FCCP are (1) when the fusion protein is recombinantly expressed in a host system, the separation and purification process can be conducted in high concentration of chaotropic agents in one or more steps, such as up to 10M urea or Gu.HCl can be used in the purification process, preferably from 4M-8M for urea and 3-6M for Gu.HCl; (2) the purified homogenous FCCP will be refolded with a process involving gradually removing out chaotropic agents presented in the purified sample; (3) in the refolding process, FCCP will self-assemble into macro-molecular structures containing multi-FCCP subunits, the assembled macro-molecular structures can be a VLP structure or another structure with totally different morphology; (4) the macro-molecular structures can be used as antigen or epitope delivery systems, such as protein or peptide based antigens or epitopes can be fused to the FCCP by recombinant DNA method to produce peptide bond linked fusion proteins, or can be chemically linked or conjugated to the FCCP; the purified FCCP can be used to incorporate desired moieties, e.g., nucleic acids, proteins, peptides, hormones, anti-cancer agents and antiviral agents into the macro-molecular structures during reassembly. In the FCCP molecules, capsid protein is the component mainly responsible for the formation of macro-molecule structures because of its intrinsic self-assembly ability, chaperone protein is the component providing the possibility to process FCCP in denatured form with the incorporation of high concentration of chaotropic agents in the purification process and subsequently refold and reassembly. The denatured capsid protein alone often forms aggregates in the refolding process, and very often, the denatured capsid protein can not stay in non-denaturing solution in soluble forms because of the formation of the aggregates. The possible mechanism might be related to the hydrophobic patches in capsid proteins. Hydrophobic patches in capsid proteins are critical in self-assembling and maintaining the VLP structures, and they are buried inside of the capsid proteins in the VLP structures (69-74). In the high concentration of denaturant solutions, such as urea or Gu.HCl solutions, capsid proteins are denatured and the buried hydrophobic patches are exposed to the solutions. When denaturants are gradually removed from the solutions in the refolding process, the gradually increased interaction among the exposed hydrophobic patches make the capsid proteins forming aggregates. When FCCP subjected to the high concentration of urea or Gu.HCl, the hydrophobic patches in capsid protein are exposed to the solutions too, but when denaturants are gradually removed from the solutions in the refolding process, the exposed hydrophobic patches in capsid proteins can be protected by fused chaperone protein, and the FCCP can stay in solutions to take refolding and self-assembling process to form soluble macro-molecular structures. The FCCP is a different molecule compare to capsid protein, the refolding and in vitro assembly process are conducted by gradually removing out chaotropic agents presented in the denatured preparation of FCCP, which are fundamentally different from the nature process of capsid protein's folding and self-assembly into VLPs. Because of above reasons, the morphology of the macro-molecular structures prepared from this invention may totally differ from authentic VLPs.

One of this invention's findings is that the macro-molecular structures formed by the self-assembling of FCCP without the morphology of authentic VLPs can be very immunogenic, and may have the following advantages over authentic VLPs: (1) pre-existing immunity to authentic VLPs might be circumvented by the use of macro-molecular structures with different morphology; (2) existing immune tolerance to authentic capsid proteins might be circumvented by the use of the macro-molecular structures with different morphology; (3) the use of macro-molecular structures with different morphology might circumvent the problem of interference with commercial anti-capsid protein assays; (4) macro-molecular structures are much more stable in the solutions. The strong immunogenicity of the macro-molecular structures could be due to (1) when exogenous antigens are particulate in nature, they are presented 1,000 or 10,000-fold more efficiently than soluble antigen in both class I and class II pathways, and macro-molecule structures have features of particle antigens, (2) innate immunity might be able to recognize some conserved sequences in capsid protein in FCCP, which can work synergistically to generate strong, lasting immunological responses. Furthermore the capsid protein in the FCCP can be utilized to package nucleic acids. Some nucleic acids such as double strand RNA and unmethylated CpG-DNA are well known for their ability to greatly enhance the immune responses (75-83).

Those skilled in the art will recognize and appreciate that in the FCCP molecule, capsid protein can be a whole protein, part of the whole protein, science mutated or variant of capsid proteins which still retain the ability of self-assembly into macro-molecular structures containing multi-subunits. These variants include, but are not limited to, additions, deletions, insertions and/or substitutions of amino acids (typically 1-500, preferably 1-200, more preferably 1-50 amino acids). Those skilled in the art are able to produce the said variants of capsid proteins using published methods (106-108). Many kinds of capsid protein with the ability of self-assembly can be used in this invention. In one embodiment, said capsid protein is a human hepatitis B (HBV) core antigen. Chaperone protein can be a full length protein, a functional equivalent, such as, a fragment of whole chaperone protein, a science mutated or a variant of chaperone protein and those skilled in the art are able to produce the said functional equivalents using published methods (91-102, 104). Many chaperones are heat shock proteins, that is, proteins expressed in response to elevated temperatures or other cellular stresses (38-59, 105). The reason for this behavior is that protein folding is severely affected by heat and, therefore, some chaperones act to repair the potential damage caused by misfolding. Some chaperone proteins are involved in folding newly made proteins as they are extruded from the ribosome. There are many different families of chaperone proteins; each family acts to aid protein folding in a different way. In bacteria like *E. coli*, many of these proteins are highly expressed under conditions of high stress, for example, when placed in high temperatures. For this reason, the term "heat shock protein" has historically been used to name these chaperone proteins. The prefix "Hsp" designates that the protein is a heat shock protein.

Some of the common chaperone familys are Hsp60, Hsp70, Hsp90, Hsp 100 and small moleculae weight family of Hsp proteins (38-59). Chaperone proteins are not limited to Hsp proteins and those skilled in the art will recognize that present unknown chaperone proteins can be used to produce FCCP in the method provided in this invention when they are discovered. In one embodiment, said chaperone protein is a *M. bovis* BCG hsp65 protein (84). In this invention, the idea is to have a peptide or a protein joined to a capsid protein via a peptide bond, then the fused protein can be processed in denatured forms in one or more steps in high concentration of chaotrapic agents such as urea or Gu.HCl solution, the purified fusion protein then can be subjected to refold and self assemble process by gradually removing chaotrapoic agents out from the samples to produce macro-molecular structures.

In the FCCP, a linker may be designed between the capsid protein and the chaperone protein, and usually the linker is a peptide of 1-100 amino acids, preferably 1-50, more preferably 1-10. A specific enzyme cleavage site or chemical cleavage site may be added to the linker between the capsid protein and the chaperone protein. After the purification, refolding and assembling process, the chaperone protein might be clipped off from FCCP with a chemical method or by an enzymatic method. A specific enzyme cleavage site can be designed at the joint of the capsid protein and chaperone protein. For example asp asp asp asp lys (SEQ ID NO:1) can be recognized by enterokinase, and this sequence can be introduced into the linker of the capsid protein and chaperone protein. After refolding and reassembling, the enterokinase can be used to clip off the chaperone protein.

One of the major objects of this invention is to use the macro-molecular structures derived from FCCP instead of the VLPs derived from capsid proteins as antigen or epitope carriers for enhancing the immunogenicity of the carried epitopes or antigens for therapeutic or prophylactic vaccination.

The compositions of the macro-molecular structures derived from FCCP carrying heterologous antigen or epitope can be prepared by (1) chemically linking or conjugating heterologous antigen or epitope to the FCCP, or to the macro-molecular structures derived from FCCP; (2) linking heterologous antigen or epitope to the FCCP via a peptide bond to form a single fusion protein comprising said heterologous antigen and said FCCP. The heterologous antigen is linked to the FCCP to its N-terminal or C-terminal. Preferably the heterologous antigen is linked to the capsid protein. In this invention, said heterologous antigen may be any protein, peptide or non-peptide molecules or any of their combinations, such as a antigen or a fragment or any combination of antigens or their fragments derived from the group consisting of: (a) viruses; (b) bacteria; (c) parasites; (d) prions; (e) tumors; (f) self-molecules; (g) non-peptide hapten molecules (h) allergens; (i) hormones and (j) antigenic fragments of any of the antigens from (a) to (i); or the epitope or epitopes derived from the group consisting of: (a) viruses; (b) bacteria; (c) parasites; (d) prions; (e) tumors; (f) self-molecules; (g) allergens and (h) hormones.

In one embodiment, said heterologous antigen is E7 antigen from human papillomavirus, and the E7 antigen is linked to the N-terminal of the capsid protein of the FCCP via a peptide bond to form a fusion protein comprising E7 antigen and FCCP.

Once the capsid protein and chaperone protein are chosen, the fusion orientation is designed, and in some cases a linker is designed, then protein or peptide based antigens or epitopes can be designed to fuse to the FCCP forming single fusion protein linked by peptide bonds. Preferably, heterologous antigen or epitope is linked to the capsid protein of the FCCP as a single fusion protein. The polynucleotide comprising a nucleotide sequence encoding the designed single fusion protein can be produced by reverse translating the fusion protein sequence back to the DNA sequence. The said nucleotide sequence can be chemically synthesized or obtained by using recombinant DNA techniques or the combination of the chemical synthesis and recombinant DNA techniques. The said nucleotide sequence can be optimized to have the optimal expression in a desired host.

The said nucleotide sequence is incorporated into a suitable recombinant expression vector as a single open reading frame with necessary accessory sequences proper for its recombinant expression in a chosen system. The host cell is transformed or transfected with the expression vector. Transformed or transfected host cells are then cultured and the desired fusion protein is recombinantly expressed.

The recombinantly expressed FCCP-heterologous antigen is isolated and purified by known separation and purification methods. These methods include but are not limited to cell disruption, centrifugation, filtration, salt precipitation, column chromatography or other chromatographic methods. High concentration of chaotropic agents such as urea or Gu.HCl is (are) applied at least one step or more steps in the separation and purification process; the concentration of urea or Gu.HCl solution used in the separation and purification process can be up to 10M urea or Gu.HCl, preferably from 4M-8M for urea and 3-6M for Gu.HCl. By scouting known separation and purification methods, usually a separation and purification process can be set up to obtain highly purified sample by those skilled in the art.

The purified homogenous FCCP-heterologous antigen fusion protein is refolded and reassembled into macro-molecular structures containing multi-units of FCCP-heterologous antigen with a process involving gradually removing out chaotropic agents presented in the purified sample. There are many methods can be used for removing out chaotropic agents presented in the purified sample. These methods include but are not limited to dialysis, ultra-filtration and other methods, such as gel filtration.

The capsid protein in the FCCP-heterologous antigen fusion protein can be utilized to package nucleic acids. Some nucleic acids such as double strand RNA or unmethylated CpG-DNA are well known for their ability to greatly enhance the immune responses. Thus it is highly desirable to have double strand RNA or unmethylated CpG-DNA be packaged into the macro-molecular structures containing multi-units of FCCP-heterologous antigen by adding desired double strand RNA or unmethylated CpG-DNA into purified and denatured fusion protein of FCCP-heterologous antigen, then reassembling FCCP-heterologous antigen into macro-molecular structures by a process involving gradually removing out chaotropic agents presented in the denatured fusion protein sample.

In the FCCP heterologous antigen fusion protein, the chaperone protein is to facilitate the refolding of the denatured capsid protein, in some situations; it may be desirable to have the chaperone protein being removed after refolding and reassembling process. The composition can be prepared by another method to have the chaperone protein being removed from the final preparation using following steps.

1. Designing a fusion protein with the capsid protein linked to heterologous antigen and a chaperone protein via peptide bonds, designing an unique enzyme cleavage site at the joint of the capsid protein and the chaperone protein, the unique enzyme cleavage site is a thrombin cleavage site or an enterokinase cleavage site, or any other unique enzyme cleavage site;
2. recombinantly producing the said fusion protein containing a specific enzyme cleavage site at the joint of the capsid protein and the chaperone protein by an expression system;
3. separation and purification of the recombinantly expressed fusion protein in one or more steps in denatured form involving using high concentration of chaotropic agents, such as using up to 10M urea or Gu.HCl solutions or buffered solutions in the separation and purification process, preferably 4-8M for urea and 3-6M for Gu.HCl;
4. refolding and reassembling of the said fusion protein into macro-molecular structures by a process involving gradually removing out chaotropic agents presented in the denatured fusion protein sample;
5. clipping off the chaperone protein from the macro-molecular structures by using the desired enzyme, such as using thrombin or enterokinase;
6. separating macro-molecular structures from the clipped off chaperone protein;
7. the final macro-molecular structures comprising many subunits of mostly capsid protein fused to heterologous antigen.

The compositions of the macro-molecular structures derived from FCCP carrying heterologous antigen or epitope can also be prepared using another different approach.

The prepared heterologous antigen or epitope and macro-molecular structures prepared from FCCP or FCCP molecules can be conjugated or joined chemically using known techniques, such as, standard techniques involving covalent attachment, for example to exposed tyrosine residues or to the epsilon-amino groups of lysine residues or the carboxyl groups of aspartate and glutamate residues. The heterologous antigen and macro-molecular structures prepared from FCCP or FCCP can also be joined noncovalently by affinity interactions. Any of several known high-affinity interactions can be adapted to nonconvalently connect heterologous antigen with macro-molecular structures prepared from FCCP or FCCP. For examples, a biotin group can be added to macro-molecular structures prepared from FCCP or FCCP, the heterologous antigen can be expressed as an avidin-antigen fusion protein. The avidin-antigen fusion protein will strongly bind the biotinylated macro-molecular structures or FCCP.

The heterologous antigen can be recombinantly expressed and then purified or chemically synthesized, or separated and purified from nature sources.

Macro-molecular structures comprise FCCP can be prepared from FCCP molecules. Once the capsid protein and chaperone protein are chosen, the fusion orientation is designed, and in some cases a linker is designed, then the polynucleotide comprising a nucleotide sequence encoding the designed FCCP can be produced by reverse translating the fusion protein sequence back to the nucleotide sequence. The said nucleotide sequence can be chemically synthesized or obtained by using recombinant DNA techniques or the combination of the chemical synthesis and recombinant DNA techniques. The said nucleotide sequence can be optimized to have the optimal expression in a desired host.

The said nucleotide sequence is incorporated into a suitable recombinant expression vector as a single open reading frame with necessary accessory sequences proper for its recombinant expression in a chosen system. The host cell is transformed or transfected with the expression vector. Transformed or transfected host cells are then cultured and the desired fusion protein is recombinantly expressed.

The recombinantly expressed FCCP is isolated and purified by known separation and purification methods. These methods include but are not limited to cell disruption, centrifugation, filtration, salt precipitation, column chromatography or other chromatographic methods. High concentration of chaotropic agents such as urea or Gu.HCl is (are) applied at least one step or more steps in the separation and purification process; the concentration of urea or Gu.HCl solution used in the separation and purification process can be up to 10M urea or Gu.HCl, preferably from 4M-8M for urea and 3-6M for Gu.HCl. By scouting known separation and purification methods, usually a separation and purification process can be set up to obtain highly purified FCCP sample by those skilled in the art.

The purified homogenous FCCP is refolded and reassembled into macro-molecular structures containing multi-units of FCC with a process involving gradually removing out chaotropic agents presented in the purified sample. There are many methods can be used for removing out chaotropic agents presented in the purified sample. These methods include but are not limited to dialysis, ultra-filtration and other methods, such as gel filtration.

The capsid protein in the FCCP can be utilized to package nucleic acids. Some nucleic acids such as double strand RNA or unmethylated CpG-DNA are well known for their ability to greatly enhance the immune responses. Thus it is highly desirable to have double strand RNA or unmethylated CpG-DNA be packaged into the macro-molecular structures containing multi-units of FCCP by adding desired double strand RNA or unmethylated CpG-DNA into purified and denatured fusion protein of FCCP then reassembling FCCP antigen into macro-molecular structures by a process involving gradually removing out chaotropic agents presented in the denatured fusion protein sample.

In the FCCP, the chaperone protein is to facilitate the refolding of the denatured capsid protein, in some situations; it may be desirable to have the chaperone protein being removed after refolding and reassembling process. The composition can be prepared by another method to have the chaperone protein being removed from the final preparation using following steps.

1. Designing a FCCP fusion protein with an unique enzyme cleavage site at the joint of the capsid protein and the chaperone protein, the unique enzyme cleavage site is a thrombin cleavage site or an enterokinase cleavage site, or any other unique enzyme cleavage site;
2. recombinantly producing the said fusion protein containing a specific enzyme cleavage site at the joint of the capsid protein and the chaperone protein by an expression system;
3. separation and purification of the recombinantly expressed fusion protein in one or more steps in denatured form involving using high concentration of chaotropic agents, such as using up to 10M urea or Gu.HCl solutions or buffered solutions in the separation and purification process, preferably 4-8M for urea and 3-6M for Gu.HCl;
4. refolding and reassembling of the said fusion protein into macro-molecular structures by a process involving gradually removing out chaotropic agents presented in the denatured fusion protein sample;
5. clipping off the chaperone protein from the macro-molecular structures by using the desired enzyme, such as using thrombin or enterokinase;
6. separating macro-molecular structures from the clipped off chaperone protein;
7. the final macro-molecular structures comprising many subunits of mostly capsid protein.

Many methods are available for determining the particle size distribution of the macro-molecular structures prepared according to this invention. These methods include but are not limited to molecular sieve chromatography, ultrafiltration, using particle size measurement instrumentation from suppliers such as Malvern Instruments Ltd.

Thus, the objects of the invention are to solve the problems of the prior art and provide novel immunogenic composition comprising said macro-molecular structures, or said macro-molecular structures carrying heterologous antigen or epitope.

More specifically, it is an object of the invention to provide a novel method for utilizing capsid proteins and chaperone proteins to produce macro-molecular structures. The macro-molecular structures are self-assembled by FCCP, which is a capsid protein fused to a chaperone protein or their functional fragments fused together.

Still more specifically, it is an object of the invention to use the macro-molecular structures as antigen carriers for eliciting enhanced immune responses, particularly cell-mediated immune response against carried antigens or epitopes. Such as, protein or peptide based antigens or epitopes can be fused to the FCCP by recombinant DNA method, or desired antigens or epitopes can be chemically linked or conjugated to the FCCP, or desired antigens or epitopes can also be joined noncovalently by affinity interactions.

It is also an object of the invention to provide a method which enables the purification of FCCP in one or more steps in denatured form using high concentration of chaotropic agents such as urea or Gu.HCl, the purified homogenous FCCP subsequently refolded and reassembled into macro-molecular structures by gradually removing chaotropic agents out from the denatured FCCP sample.

It is another object of the invention to provide a method for packaging or encapsulating desired moieties in macro-molecular structures, e.g., therapeutic or diagnostic agents.

It is still another object of the invention to provide a novel delivery system to incorporate desired moieties, e.g., nucleic acids, proteins, peptides, hormones, anti-cancer agents and antiviral agents into the macro-molecular structures during reassembly.

It is still another object of the invention to provide a novel method with the ability to prepare homogenous and well defined immunogenic compositions in a scalable process.

It is still another object of the invention to provide a novel method to prepare macro-molecular structures with the potential to circumvent pre-existing immunity to authentic VLPs.

It is still another object of the invention to provide a novel method to prepare macro-molecular structures with the potential to circumvent existing immune tolerance to authentic capsid proteins.

It is still another object of the invention to provide a novel method to prepare macro-molecular structures with the potential to circumvent the problem associated with authentic VLPs of interference with commercial anti-capsid protein based assays.

The immunogenic compositions of this invention described above, are preferably used for therapeutic vaccination. However, the compositions may also be used for prophylactic vaccination. The compositions of this invention are suitable for injection and routes and procedures of administration include, but are not limited to standard intramuscular, subcutaneous, intradermal, intravenous, oral or rectal routes and procedures. In addition, the compositions of this invention can contain and be administered together with other pharmacologically acceptable components. The compositions of this invention can also be formulated by combining with an adjuvant or other accessory substance such as an immunostimulatory molecule in order to enhance its effect as a therapeutic vaccine, and also to stimulate a preferred type of immune response in the recipient host. Useful adjuvant include, but are not limited to: double strand RNA, unmethylated CpG-DNA, aluminum hydroxide. Such adjuvant and/or other accessory substances can be used separately or in combinations as desired.

The amount of the compositions in this invention used for therapeutic or prophylactic purposes is an amount which can induce effective immune responses in a subject when administered. In addition, the amount of the compositions administered to the subject will vary depending on a variety of factors, including but not limiting to: the formulation of the compositions, adjuvant and its amount, the size, age, body weight, sex, general health and immunological responses of the subject. Effective amounts can be determined in subjects and adjustment and manipulation of established dose range are well within the ability of those skilled in the art. For example, the effective amount of compositions can be from 0.1 microgram to about 10 milligrams for per kilogram body weight, preferably from 1 microgram to 1 milligram for per kilogram body weight. One or more doses of the vaccine may be administered at intervals. This regime can readily be optimized in subjects by those skilled in the art.

The following examples are provided in order to demonstrate and further illustrate the present invention, and are not to be construed as limiting the scope thereof.

EXAMPLES

Example 1

FCCP Molecule Carrying an HPV Antigen

A chaperone protein-Hsp65 derived from *Mycobacterium bovis* BCG hsp65 gene (84) is fused to the C-terminal of the nucleocapsid protein (core antigen) of Hepatitis B virus (HBV) subtype ADW2 (85-86) to form a FCCP molecule. An E7 antigen from human papillomavirus type 16 (87) is fused to the N-terminal of the FCCP molecule. The single fusion protein starting from N-terminal is E7 protein, the C-terminal of E7 antigen is fused to the N-terminal of capsid protein, and the C-terminal of capsid protein is fused to the N-terminal of Hsp65 protein. The fusion protein has theoretic molecular weight of 89.2 KD, and is represented as E7-Core-Hsp65. The DNA sequence encoding E7-Core-Hsp65 fusion protein was chemically synthesized according to DNA sequences from GenBank (86-87, 110) without any variations.

The synthesized DNA sequence was named Ankegens 2479 bp and cloned into SmaI digested pBluescript II SK (+/−) from Stratagene (88) to produce pBSK-Ankegens-2479 bp.

Example 2

Expression and Purification of E7-Core-Hsp65 Fusion Protein

E7-Core-BCG65 DNA fragment was cut from pBSK-Ankegens-2479 bp by NdeI and EcoRI then subcloned into pET-23a (89) corresponding sites to produce pET-23a-2479. The pET-23a-2479 was transformed into Rosetta-gami (DE3) from Novagen. E7-Core-BCG65 fusion protein was expressed in *E. coli* cells by fermentation and induction of transformed Rosetta-gami (DE3) cells with 0.5 mM isopropyl-thio-galatopyranoside according to Novagen's pET System Manual. After fermentation, cells were harvested by centrifugation. Cells were washed once by suspending 100 g cell paste in 1000 ml of buffer A (100 mM Tris-Hcl pH 9.0; 5 mM EDTA) then centrifuging at 8500 rpm for 30 minutes. Discarded the supernatant then re-suspended the pelleted cells with 1000 ml of buffer B (50 mM sodium acetate; 2 mM EDTA). The suspended cells were ruptured by homogenization process with pressure at 760 bar, and then centrifuged at 8500 rpm for 30 minutes. The supernatant was collected and the volume was measured. Urea was added to the supernatant according to 0.7 g urea for 1 ml supernatant, and then sodium chloride was added to final concentration at 100 mM, L-Cysteine was added to final concentration at 20 mM. The solution was stirred at room temperature to have all the urea dissolved then stirred at 4° C. for overnight. After overnight stirring, the sample was applied to an XK-50 column (GE Health) containing 300 ml of SP-Sepharose resin (GE Health), which was previously washed with 1 M sodium chloride and equilibrated with buffer C (50 mM sodium acetate; 100 mM NaCl; 2 mM EDTA; 8M urea; 10 mM L-Cysteine). After sample loading, the column was washed with 10 column-volumes of buffer D (50 mM sodium acetate; 100 mM NaCl; 2 mM EDTA; 8M urea; 10 mM L-Cysteine; 2.5% Triton-X-100) overnight to remove endotoxin. After overnight washing with buffer D, the column was washed with 5 column-volumes of buffer C to remove Triton-X-100, and then the column was washed with 3 column-volumes of buffer E (50 mM sodium acetate; 300 mM NaCl; 2 mM EDTA; 8M urea; 10 mM L-Cysteine) to remove contaminations. E7-Core-BCG65 fusion protein was eluted from the column with buffer D (50 mM sodium acetate; 800 mM NaCl; 2 mM EDTA; 8M urea; 10 mM L-Cysteine). Pooled eluted protein was dialyzed against 4×40 volumes of buffer F (50 mM sodium acetate, 6Murea) to remove NaCl and L-Cysteine. After dialysis, Oxidative sulfitolysis was performed by adding sodium sulfite and sodium tetrathionate to final concentrations of 200 mM and 50 mM respectively and incubating for overnight at room temperature. The sulfitolyzed sample was diluted 5 volumes with buffer F then applied to an XK-50 column with 150 ml of Q-Sepharose resin (GE Health), which was previously washed with 1M NaCl and equilibrated with buffer F. After sample loading, the column was washed with 2 column-volumes of 95% buffer F and 5% buffer G (50 mM sodium acetate; 1M NaCl; 6Murea), and then E7-Core-BCG65 fusion protein was eluted with a lineal gradient from 95% buffer F and 5% buffer G to 50% buffer F and 50% buffer G over 8 column-volumes. Eluted E7-Core-BCG65 fusion protein was pooled, and then dialyzed against 1×40 volumes of Tris.HCl pH9.0, 1×40 volumes of Tris.HCl pH7.5 with 100 mM NaCl to remove urea and refold E7-Core-BCG65 fusion protein. The endotoxin levels in the final preparations (E7-Core-BCG65 in Tris.HCl pH7.5 with 100 mM NaCl) were below 5 EU/mg protein.

SDS-PAGE shows that the purified sample contains a single major band migrating closely under 97.4 Kd marker. The purified sample was subjected to N-terminal amino acid sequencing, and the determined N-terminal amino acid sequence was MHGDTPTLHEYMLD (SEQ ID NO:2), which matched the theoretic N-terminal sequence of E7-Core-BCG65. Based on SDS-PAGE and N-terminal sequencing results, the purified sample was confirmed to be E7-Core-BCG65 fusion protein.

The particle size distribution of refolded E7-Core-BCG65 was analyzed by Malvern Zetasizer Nano ZS from Malvern Instruments Ltd. The measured sample had Z-Average size: 61.3 nm, PDI<0.2, result quality: good.

The molecular sieve chromatography was used to compare relative molecular mass among refolded E7-Core-BCG65, bovine serum albumin (BSA, a monomer protein with molecular weight 67 Kd) and authentic VLPs prepared from recombinantly expressed L1 capsid protein of human papillomavirus (Wison Bioengineering Ltd. Shanghai). The column's diameter is 1.5 cm; column volume is 180 ml Sepharose 4B FF (GE Healthcare); running buffer is 100 mM PB, 0.4M NaCl, pH6.5; flow rate is 2 ml/min; sample volume is 1 ml for each sample. The refolded E7-Core-BCG65 was eluted with elution volume of 70 ml, which was the same as authentic VLPs from HPV L1 capsid protein, and the elution volume of the BSA was close to 150 ml.

The refolded E7-Core-BCG65 was amorphous structure under the electro-microscope.

In Western blotting experiment, the antibody against hepatitis B virus core antigen from Abcam failed to detect core antigen of refolded E7-Core-BCG65, and the result might indicate that the sample can be administered to a host with pre-existing anti HBV immune responses.

Example 3

Therapeutic and Prophylactic Effects of E7-Core-BCG65 Treatment in Mice

The E7-Core-BCG65 is an FCCP carrying an E7 antigen from HPV type 16, and the E7 expressing TC-1 tumor cells were used to evaluate the therapeutic and prophylactic applications of E7-Core-BCG65 on mice bearing TC-1 tumor or being challenged with TC-1 tumor.

Female C57BL/6 mice, six to eight weeks old (20.0±2.0 g) were purchased from SHANGHAI SLAC LABORATORY ANIMAL CO. LTD. Quality Control No.: SCXK (Shanghai) 2003-0003.

TC-1 cell line expressing HPV16 E7 protein was derived from primary lung cells of C57BL/6 mice by immortalization and transformation with HPV 16 E7 gene and an activated human C-Ha-ras gene as described in Lin et al. (90). TC-1 cells were grown in RPMI1640 medium supplemented with 10% fetal calf serum, 2 mM nonessential amino acids, 2 mM L-glutamine, 1 mM pyruvate, Penicillin/Streptomycin, and the cells were harvested by trypsinization, the cells were washed three times with PBS then re-suspended in PBS. $1 \times 10^5$ TC-1 cells were inoculated subcutaneously into the mice and the mice were treated with E7-Core-BCG65 or saline subcutaneously according to their experiment groups.

Animal Experiment Groups:

| Groups | Mice | Dose Treatment | Time of E7-Core-BCG65 Treatment |
|---|---|---|---|
| Therapeutic Application | 8 | 500 ug E7-Core-BCG65 | 48 h and 16 days after inoculation of TC-1 |
| | 8 | 100 ug E7-Core-BCG65 | 48 h and 16 days after inoculation of TC-1 |
| | 8 | 20 ug E7-Core-BCG65 | 48 h and 16 days after inoculation of TC-1 |
| Prophylactic Application | 8 | 100 ug E7-Core-BCG65 | Two treatments with 14 days in between Inoculation of TC-1 14 days after second treatment |
| | 8 | 20 ug E7-Core-BCG65 | Two treatments with 14 days in between Inoculation of TC-1 14 days after second treatment |
| Control | 6 | Saline | 48 h and 16 days after inoculation of TC-1 |

The mice were monitored for the presence or absence of tumor by palpation and the volume of the tumor was measured with Vernier Caliber by 2 orthogonal dimensions twice a week; these measurements were extrapolated to mm3 and are presented as average tumor volume±standard error of the mean. The life span of the mice was recorded.

In control group, the presence of the tumor was observed 4 days after TC-1 inoculation; the average volume of the tumor was grown to 40 mm3 10 day after inoculation and 7499.84 mm3 36 days after inoculation. All mice in the control group died within 60 days after inoculation.

In therapeutic group, mice were treated with E7-Core-BCG65 48 h and 16 days after TC-1 inoculation; the average volume of the tumor was grown to 181.89 mm3 (500 ug), 671.34 mm3 (100 ug) and 2148.57 mm3 (20 ug) 36 days after inoculation. All mice were alive 60 days after inoculation.

In the prophylactic group, mice were treated with E7-Core-BCG65 twice in 14 days, and after second treatment, mice were inoculated with TC-1; the average volume of the tumor was grown to 22.43 mm3 (100 ug) and 89.08 mm3 (20 ug) 36 days after inoculation. All mice were alive 60 days after inoculation.

TABLE 1

The average tumor volume in different experiment groups (mm³) ($\bar{x} \pm s$)

| Date (day) | Therapeutic Group | | | Prophylactic Group | | Control Group |
|---|---|---|---|---|---|---|
| | 500 ug (n = 8) | 100 ug (n = 8) | 20 ug (n = 8) | 100 ug (n = 8) | 20 ug (n = 8) | (n = 6) |
| 10 | 8.65 ± 5.40 | 16.33 ± 8.83 | 42.54 ± 24.55* | 2.32 ± 1.06 | 5.56 ± 2.91 | 39.00 ± 19.28 |
| 13 | 41.70 ± 20.90 | 51.01 ± 20.37 | 84.72 ± 36.72* | 1.97 ± 2.44 | 10.58 ± 25.56 | 133.57 ± 69.64 |
| 16 | 31.91 ± 12.26 | 49.96 ± 20.62 | 189.07 ± 91.07* | 1.97 ± 1.42 | 5.24 ± 2.08 | 320.20 ± 149.14 |
| 19 | 35.69 ± 10.52 | 156.28 ± 46.49 | 208.49 ± 85.46 | 2.85 ± 1.49 | 25.65 ± 10.43 | 782.65 ± 257.69 |
| 22 | 43.89 ± 21.13 | 224.71 ± 107.46 | 357.47 ± 159.47 | 2.44 ± 1.98 | 35.24 ± 80.41 | 1033.81 ± 594.12 |
| 25 | 109.04 ± 47.41 | 257.01 ± 107.19 | 756.40 ± 258.40 | 4.52 ± 2.78 | 17.38 ± 6.76 | 2414.19 ± 1201.87 |
| 28 | 127.68 ± 56.24 | 395.56 ± 128.72 | 892.54 ± 364.47 | 18.81 ± 5.42 | 69.63 ± 24.46 | 4432.67 ± 1824.46 |
| 31 | 156.12 ± 49.46 | 525.81 ± 152.94 | 1527.21 ± 510.46 | 20.57 ± 10.46 | 85.57 ± 25.85 | 6024.54 ± 2465.46 |
| 34 | 181.89 ± 75.53 | 671.34 ± 301.28 | 2048.57 ± 1050.57 | 22.42 ± 18.60 | 89.08 ± 43.09 | 7499.84 ± 3722.56 |
| 37 | 250.52 ± 120.59 | 785.69 ± 268.85 | 3051.65 ± 1253.32 | 56.83 ± 25.56 | 173.59 ± 89.41 | 9483.58 ± 4565.74 |
| 40 | 396.88 ± 208.12 | 921.87 ± 368.03 | 3887.08 ± 1889.08 | 59.81 ± 26.79 | 173.92 ± 86.39 | 13141.43 ± 5077.39 |

Those skilled in the art will recognize, or be able to ascertain that the basic construction in this invention can be altered to provide other embodiments which utilize the process of this invention. Therefore, it will be appreciated that the scope of this invention is to be defined by the claims appended hereto rather than the specific embodiments which have been presented hereinbefore by way of example.

The invention claimed is:

1. An immunogenic composition comprising macro-molecular structures containing multi-units of fusion protein comprising a capsid protein, a chaperone protein and a desired antigen or antigens or epitope(s) joined together by peptide bond(s); wherein the said capsid protein has the intrinsic ability of self-assembling into virus-like particles; and the said macro-molecular structures are obtained by: (a) recombinantly producing the said fusion protein comprising a capsid protein, a chaperone protein and a desired antigen(s) joined together by peptide bonds by an expression system; (b) separating and purifying of said fusion protein in the presence of chaotropic agent, thereby obtaining purified fusion protein in denatured form; (c) refolding and reassembling of the denatured fusion protein into macro-molecular structures containing multi-units of fusion protein by a process involving removing out chaotropic agents presented in the denatured fusion protein sample; the said macro-molecular structures are morphologically different from a virus or virus-like particles; wherein the said macro-molecular structures induce immune responses to said desired antigen(s) in a mammal to whom the macro-molecular structures are administered.

2. An immunogenic composition comprising macro-molecular structures containing multi-units of fusion protein comprising a capsid protein and a chaperone protein joined together via a peptide bond, and a desired antigen or antigens or epitope(s) joined to the fusion protein by chemical linking, or conjugation(s), or non-covalent linking by affinity interactions; wherein the said capsid protein has the intrinsic ability of self-assembling into virus-like particles; and the said macro-molecular structures are obtained by: (a) recombinantly producing the said fusion protein comprising a capsid protein and a chaperone protein joined together by a peptide bond by an expression system; (b) separating and purifying of said fusion protein in the presence of chaotropic agent, thereby obtaining purified fusion protein in denatured form; (c) refolding and reassembling of the fusion protein into macro-molecular structures containing multi-units of fusion protein by a process involving removing out chaotropic agents presented in the denatured fusion protein sample; (d) chemically linking or conjugating desired antigen(s) to the macro-molecular structures, or linking the desired antigen(s) to the macro-molecular structures by affinity interactions; the said macro-molecular structures are morphologically different from a virus or virus-like particles; wherein the said macro-molecular structures induce immune responses to said desired antigen(s) in a mammal to whom the macro-molecular structures are administered.

3. An immunogenic composition comprising macro-molecular structures containing multi-units of fusion protein comprising a capsid protein and a chaperone protein joined together via a peptide bond, and a desired antigen or antigens or epitope(s) joined to the fusion protein by chemical linking, or conjugation(s); wherein the said capsid protein has the intrinsic ability of self-assembling into virus-like particles; and the said macro-molecular structures are obtained by: (a) recombinantly producing the said fusion protein comprising a capsid protein and a chaperone protein joined together by a peptide bond by an expression system; (b) separating and purifying of said fusion protein in the presence of chaotropic agent, thereby obtaining purified fusion protein in denatured form; (c) chemically linking or conjugating desired antigen to the denatured fusion protein; (d) refolding and reassembling of the fusion protein into macro-molecular structures containing multi-units of fusion protein with linked or conjugated desired antigen by a process involving removing out chaotropic agents presented in the denatured fusion protein sample; the said macro-molecular structures are morphologically different from a virus or virus-like particles; wherein the said macro-molecular structures induce immune responses to said desired antigen(s) in a mammal to whom the macro-molecular structures are administered.

4. The composition of any one of claims 1-3, wherein the capsid protein is from: (a) an animal virus, (b) a bacterium virus, (c) a yeast virus.

5. The composition of any one of claims 1-3, wherein the capsid protein is the core antigen from Hepatitis B virus.

6. The composition of any one of claims 1-3, wherein the chaperone protein is from a member of the chaperone families.

7. The composition of any one of claims 1-3, wherein the chaperone protein is the *Mycobacterium bovis* BCG Hsp65 protein.

8. The composition of any one of claims 1-3, wherein the antigen is an antigen or a fragment thereof, or a combination of antigens or fragments thereof, selected from the group consisting of a virus, a bacterium, a parasite, a prion, a tumor, a self-molecule, a non-peptide hapten, an allergen and a hormone, wherein the antigen comprises one or more epitopes.

9. The composition of any one of claims 1-3, wherein the antigen is an E7 antigen from human papillomavirus type 16.

10. A method of preparation of the composition of claim 1, comprising the steps of:
    a) recombinantly producing the fusion protein comprising a capsid protein, a chaperone protein and a desired antigen(s) joined together by peptide bonds by an expression system;
    b) separating and purifying of said fusion protein in the presence of chaotropic agent, thereby obtaining purified fusion protein in denatured form;
    c) refolding and reassembling of the denatured fusion protein into macro-molecular structures containing multi-units of fusion protein by a process involving gradually removing out chaotropic agents presented in the denatured fusion protein sample.

11. A method of preparation of the composition of claim 2, comprising the steps of:
    a) recombinantly producing the fusion protein comprising a capsid protein and a chaperone protein joined together by a peptide bond by an expression system;
    b) separating and purifying of said fusion protein in the presence of chaotropic agent, thereby obtaining purified fusion protein in denatured form;
    c) refolding and reassembling of the fusion protein into macro-molecular structures containing multi-units of fusion protein by a process involving removing out chaotropic agents presented in the denatured fusion protein sample;
    d) chemically linking or conjugating desired antigen(s) to the macro-molecular structures, or non-covalently linking the desired antigen(s) to the macro-molecular structures by affinity interactions.

12. A method of preparation of the composition of claim 3, comprising the steps of:
    a) recombinantly producing the fusion protein comprising a capsid protein and a chaperone protein joined together by a peptide bond by an expression system;
    b) separating and purifying of said fusion protein in the presence of chaotropic agent, thereby obtaining purified fusion protein in denatured form;
    c) chemically linking or conjugating desired antigen(s) to the denatured fusion protein
    d) refolding and reassembling of the fusion protein into macro-molecular structures containing multi-units of fusion protein with linked or conjugated desired antigen(s) by a process involving removing out chaotropic agents presented in the denatured fusion protein sample.

13. The method of any one of claims 10-12, wherein step (b) involves using up to 10M urea or 8M guanidine hydrochloride.

14. A composition comprising:
    a) the composition set forth in any one of claims 1-3, and
    b) at least one immunostimulatory substance.

15. The composition of claim 14, wherein said immunostimulatory substance is an unmethylated CpG-containing oligonucleotide, or a double strand RNA molecule, or aluminum hydroxide, or aluminum salt.

16. A method of generating an immune response in a host against a desired antigen(s), comprising the step of administering an effective amount of the composition from any one of claims 1-3 to a subject.

17. A method of generating immune responses in a host against E7 antigen from human papillomavirus, comprising the step of administering an effective amount of the composition of claim 9 to a subject.

18. A composition comprising:
a) the composition set forth in claim 4, and
b) at least one immunostimulatory substance.

19. A composition comprising:
a) the composition set forth in claim 5, and
b) at least one immunostimulatory substance.

20. A composition comprising:
a) the composition set forth in claim 6, and
b) at least one immunostimulatory substance.

21. A composition comprising:
a) the composition set forth in claim 7, and
b) at least one immunostimulatory substance.

22. A composition comprising:
a) the composition set forth in claim 8, and
b) at least one immunostimulatory substance.

23. A composition comprising:
a) the composition set forth in claim 9, and
b) at least one immunostimulatory substance.

24. The composition of claim 18, wherein said immunostimulatory substance is an unmethylated CpG-containing oligonucleotide, or a double strand RNA molecule, or aluminum hydroxide, or aluminum salt.

25. The composition of claim 19, wherein said immunostimulatory substance is an unmethylated CpG-containing oligonucleotide, or a double strand RNA molecule, or aluminum hydroxide, or aluminum salt.

26. The composition of claim 20, wherein said immunostimulatory substance is an unmethylated CpG-containing oligonucleotide, or a double strand RNA molecule, or aluminum hydroxide, or aluminum salt.

27. The composition of claim 21, wherein said immunostimulatory substance is an unmethylated CpG-containing oligonucleotide, or a double strand RNA molecule, or aluminum hydroxide, or aluminum salt.

28. The composition of claim 22, wherein said immunostimulatory substance is an unmethylated CpG-containing oligonucleotide, or a double strand RNA molecule, or aluminum hydroxide, or aluminum salt.

29. The composition of claim 23, wherein said immunostimulatory substance is an unmethylated CpG-containing oligonucleotide, or a double strand RNA molecule, or aluminum hydroxide, or aluminum salt.

30. A method of generating an immune response in a host against a desired antigen(s), comprising the step of administering an effective amount of the composition of claim 18 to a subject.

31. A method of generating an immune response in a host against a desired antigen(s), comprising the step of administering an effective amount of the composition of claim 19 to a subject.

32. A method of generating an immune response in a host against a desired antigen(s), comprising the step of administering an effective amount of the composition of claim 20 to a subject.

33. A method of generating an immune response in a host against a desired antigen(s), comprising the step of administering an effective amount of the composition of claim 21 to a subject.

34. A method of generating an immune response in a host against a desired antigen(s), comprising the step of administering an effective amount of the composition of claim 22 to a subject.

35. A method of generating an immune response in a host against a desired antigen(s), comprising the step of administering an effective amount of the composition of claim 23 to a subject.

36. A method of generating an immune response in a host against a desired antigen(s), comprising the step of administering an effective amount of the composition of claim 24 to a subject.

37. A method of generating an immune response in a host against a desired antigen(s), comprising the step of administering an effective amount of the composition of claim 25 to a subject.

38. A method of generating an immune response in a host against a desired antigen(s), comprising the step of administering an effective amount of the composition of claim 26 to a subject.

39. A method of generating an immune response in a host against a desired antigen(s), comprising the step of administering an effective amount of the composition of claim 27 to a subject.

40. A method of generating an immune response in a host against a desired antigen(s), comprising the step of administering an effective amount of the composition of claim 28 to a subject.

41. A method of generating an immune response in a host against a desired antigen(s), comprising the step of administering an effective amount of the composition of claim 29 to a subject.

* * * * *

```
SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Asp Asp Asp Asp Lys
1               5

<210> SEQ ID NO 2
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(14)
<223> OTHER INFORMATION: N-terminal amino acid sequence

<400> SEQUENCE: 2

Met His Gly Asp Thr Pro Thr Leu His Glu Tyr Met Leu Asp
1               5                   10
```